(12) United States Patent
Murao et al.

(10) Patent No.: US 7,050,613 B2
(45) Date of Patent: May 23, 2006

(54) METHOD FOR SUPPORTING CELL IMAGE ANALYSIS

(75) Inventors: Kohei Murao, Kawasaki (JP); Shuji Suda, Kawasaki (JP); Hitohide Usami, Kawasaki (JP); Masatoshi Naruse, Oita (JP); Toshiyuki Gotoh, 4-18-505, Yashio 5-chome, Shinagawa-ku, Tokyo 140-0003 (JP); Seiichirou Kagei, 34-7, Nakazawa 2-chome, Asahi-ku, Yokohama-shi, Kanagawa 241-0814 (JP); Noriko Kabuyama, 28-B-1409, Deiki 1-chome, Kanazawa-ku, Yokohama-shi, Kanagawa 236-0021 (JP)

(73) Assignees: Fujitsu Limited, Kawasaki (JP); Toshiyuki Gotoh, Tokyo (JP); Seiichirou Kagei, Yokohama (JP); Noriko Kabuyama, Yokohama (JP)

( * ) Notice: Subject to any disclaimer, the term of this patent is extended or adjusted under 35 U.S.C. 154(b) by 0 days.

(21) Appl. No.: 11/089,223

(22) Filed: Mar. 25, 2005

(65) Prior Publication Data

US 2005/0163359 A1    Jul. 28, 2005

Related U.S. Application Data

(63) Continuation of application No. PCT/JP02/11624, filed on Nov. 7, 2002.

(51) Int. Cl.
    *G06K 9/00* (2006.01)

(52) U.S. Cl. .................................. 382/128; 382/133
(58) Field of Classification Search ........ 382/128–134; 358/598; 356/39
See application file for complete search history.

(56) References Cited

U.S. PATENT DOCUMENTS

| 4,761,075 A | * | 8/1988 | Matsushita et al. ............ 356/39 |
| 4,812,909 A | * | 3/1989 | Yokobayashi et al. ...... 348/589 |
| 5,162,990 A | * | 11/1992 | Odeyale et al. ............. 382/128 |

FOREIGN PATENT DOCUMENTS

| EP | 549905 | 7/1993 |
| JP | 53-52494 | 5/1978 |
| JP | 64-47948 | 2/1989 |
| JP | 5-249102 | 9/1993 |
| JP | 3224860 | 8/2001 |

* cited by examiner

*Primary Examiner*—Duy M. Dang
(74) *Attorney, Agent, or Firm*—Staas & Halsey LLP

(57) ABSTRACT

A fluorescent image, and either a bright-field image or a phase difference image of a plurality of cells are acquired by a microscope. A position of each cell is specified in the fluorescent image, and then a cell region of each cell is specified using the bright-field image or the phase difference image. A fluorescent part other than the cell region is thereby excluded. A class of each cell is determined, that is, the cells are classified. Thereafter, based on these results, a report is created.

12 Claims, 20 Drawing Sheets

FIG.20
| IMAGE EXAMPLE | CLASS NAME | CLASS ABBREVIATION | IMAGE EXAMPLE | CLASS NAME | CLASS ABBREVIATION |
|---|---|---|---|---|---|
| 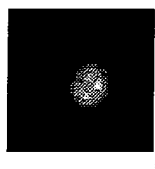 | cytoplasm | Cyto |  | nucleolus | Nuc |
| 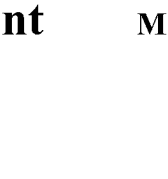 | Golgi | Gol | | nucleus | N |
| 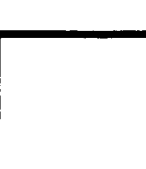 | mitochondria | Mito | | microtubules | Tub |
|  | peroxisomes | Per | | endosome | Endo |
|  | endoplasmic reticulum | ER | | actin filament | Actin |
|  | membrane | Mem | | | |

METHOD FOR SUPPORTING CELL IMAGE ANALYSIS

This application is a continuing application, filed under 35 U.S.C. §111(a), of International Application PCT/JP02/11624, filed Nov. 7, 2002.

BACKGROUND OF THE INVENTION

1) Field of the Invention

The present invention relates to a genome analysis on a cell image photographed by a microscope or the like for biotechnological research and development, drug manufacturing, and the like. More specifically, the present invention relates to efficiency improvement in the analysis by automatically clipping images of each cell from the cell image, specifying types of each cell, and displaying the images and the types of each cell as a list.

2) Description of the Related Art

Recently, following an advancement of genome science, a study of identifying a protein localization pattern and observing a morphogenetic change for a cell into which a cDNA is injected, that is, a study of identifying functions of a DNA by performing a quantitative analysis on a morphogenetic change induced by injection of the cDNA into the cell is conducted. There is, for example, a demand for determining gene expressions, determining a class of a protein localization pattern, and performing a screening to determine how a cell changes by injecting a gene into the cell so as to confirm pharmaceutical effects.

To meet such a demand, therefore, a change in a stained or fluorescently colored cell is observed by a microscope. A system that automatically captures an image during the observation is conventionally put to practical use. These conventional techniques, by means of a plate on which many wells (holes) are arranged for cell cultivation, enable cells to be cultured in large quantities and to be observed and screened by the microscope.

A microscope-based image capturing apparatus HTS-50 manufactured by Matsushita Electric Industrial Co., Ltd is one example of a product. The apparatus has a function of calculating quantitative and numeric values such as a flatness of a cell, a length of a neurite, and a stained nucleus from cell images. However, the apparatus does not analyze individual cells but a texture of an entire image or a total extension of elongate structures. Besides, the system is generally manufactured on the premise that an experimenter visually checks all raw images. On the other hand, Beckman Coulter Inc. (United States) put into practical use an apparatus and an application for analyzing microscope images. Similarly to the HTS-50, the apparatus and application of Beckman Coulter are provided on the premise that an experimenter visually checks the images.

Further, Japanese PatentApplication Laid-open No. H5-249102 is one example of the conventional techniques.

These conventional techniques have, as described above, a disadvantage of a need for a person to visually check images one by one in a screening. With such a method for visually checking an experimental result and extracting individual cell regions manually, it is disadvantageously, extremely difficult to process images in large quantities generated in experiments conducted for multiple cDNAs.

Specifically, although it suffices to obtain one result from one well, several images to several tens of images are actually generated from one well. Since about one hundred wells are used in one experiment, several hundreds to several thousands of images are generated in one experiment. Besides, even if the images are displayed with reduced sizes, a necessary cell region occupies only a small area (for example, 1/400) of the image. The images cannot be, therefore, displayed as a list without processing them. Moreover, a success probability of injecting cDNAs into cells depends on a type of a target cell, a type of a cDNA, or a property of a culture medium, and sometimes the injection is successful only one cell in a hundred cells. Thus, since the cells in which the cDNA is injected are present only sporadically, it disadvantageously takes lots of time and labor to locate these cells and to manually name each protein localization pattern and each cellular morphogenesis.

Furthermore, to analyze images and display a result, a uniform processing is conventionally performed on entire images. Therefore, the result is often displayed for each image. Since the success probability of the cDNA injection is low in cDNA experiments, it is necessary to discriminate cells injected with cDNAs from those non-injected with cDNAs. Further, because of multiple types of fluorescent patterns and a feeble pattern in a background, such as a noise, it is disadvantageously difficult to discriminate each cell pattern from the background. In some cases, all cells are fluorescently colored. In other cases, a part of cells are fluorescently colored in a grainy manner. If the adjacent cells are entirely fluorescently colored, they need to be separated from each other. If the cells are fluorescently colored in a grainy manner, it is necessary to recognize a dark part between grains so as not to regard it as the background. Thus, even if the experimenter visually checks the result, it is often difficult to make a clear determination. As a result, it is disadvantageously impossible to improve experimental and analytical efficiencies.

SUMMARY OF THE INVENTION

It is an object of the present invention to at least solve the problems in the conventional technology.

An image analysis supporting method according to an aspect of the present invention includes accepting an input of a fluorescent image of a plurality of cells adhering to a well of a well plate, and an input of any one of a bright-field image and a phase difference image or both that are equal in field of view to the fluorescent image; detecting a position of each cell in the fluorescent image; determining a class of each cell the position of which is detected; and outputting a list that includes information on the class and an image of each cell that is clipped from any one of the bright-field image and the phase difference image on the basis of the position.

A computer-readable recording medium according to another aspect of the present invention stores a computer program that causes a computer to execute: accepting an input of a fluorescent image of a plurality of cells adhering to a well of a well plate, and an input of any one of a bright-field image and a phase difference image or both that are equal in field of view to the fluorescent image; detecting a position of each cell in the fluorescent image; determining a class of each cell the position of which is detected; and outputting a list that includes information on the class and an image of each cell that is clipped from any one of the bright-field image and the phase difference image on the basis of the position.

An image analysis supporting device according to still another aspect of the present invention includes a first input unit that accepts an input of a fluorescent image of a plurality of cells adhering to a well of a well plate; a second input unit that accepts an input of any one of a bright-field image and a phase difference image or both that are equal in field of view to the fluorescent image; a detecting unit that detects a position of each cell in the fluorescent image; a class determining unit that determines a class of each cell the position of which is detected; and an output unit that outputs a list that includes information on the class and an image of each cell that is clipped from any one of the bright-field image and the phase difference image on the basis of the position.

The other objects, features, and advantages of the present invention are specifically set forth in or will become apparent from the following detailed description of the invention when read in conjunction with the accompanying drawings.

BRIEF DESCRIPTION OF THE DRAWINGS

FIG. 20 is exemplary images of intracellular protein localization classes.

DETAILED DESCRIPTION

Exemplary embodiments of an image analysis supporting method, a computer-readable recording medium, and an image analysis supporting device will be explained in detail with reference to the accompanying drawings.

Figure 1:
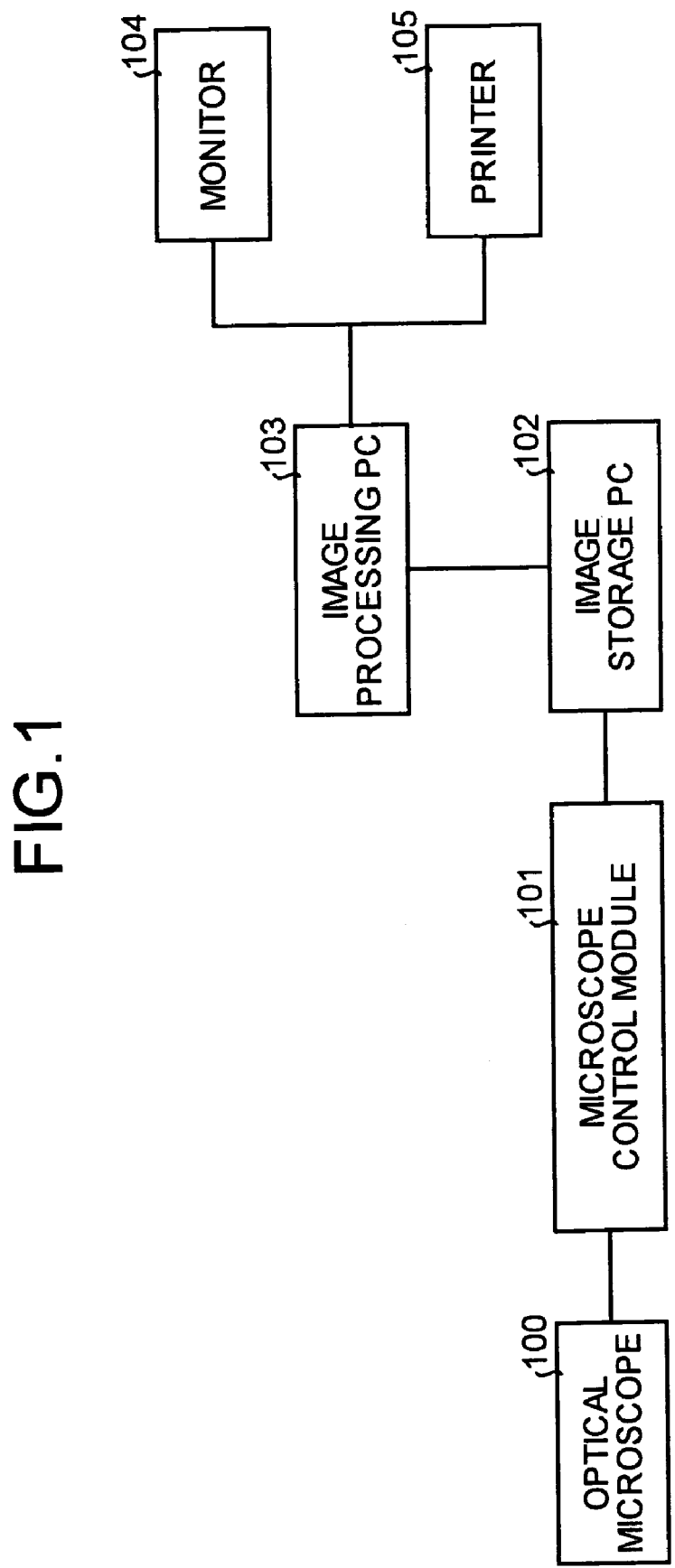
FIG. 1 is an explanatory view of one example of a hardware configuration of an image analysis supporting device according to an embodiment of the present invention.

FIG. 1 is an explanatory view of one example of the hardware configuration of an image processing apparatus according to the embodiment of the present invention.

A microscope control module 101 controls an optical microscope 100 to photograph a fluorescent image, a bright-field image, and a phase difference image. The microscope control module 101 is set so that a cell, which is successfully injected with a fluorescent marker included in the cDNA, reacts to fluorescence. The optical microscope 100 is set so that the fluorescent image, the bright-field image, and the phase difference image can be photographed in the same field of view. The microscope control module 101 includes xyz stages, a fluorescent (mercury light) shutter, a halogen light shutter, and the like, and functions of, for example, replacing a fluorescent filter and controlling a CCD camera to set an exposure time.

Figure 2:
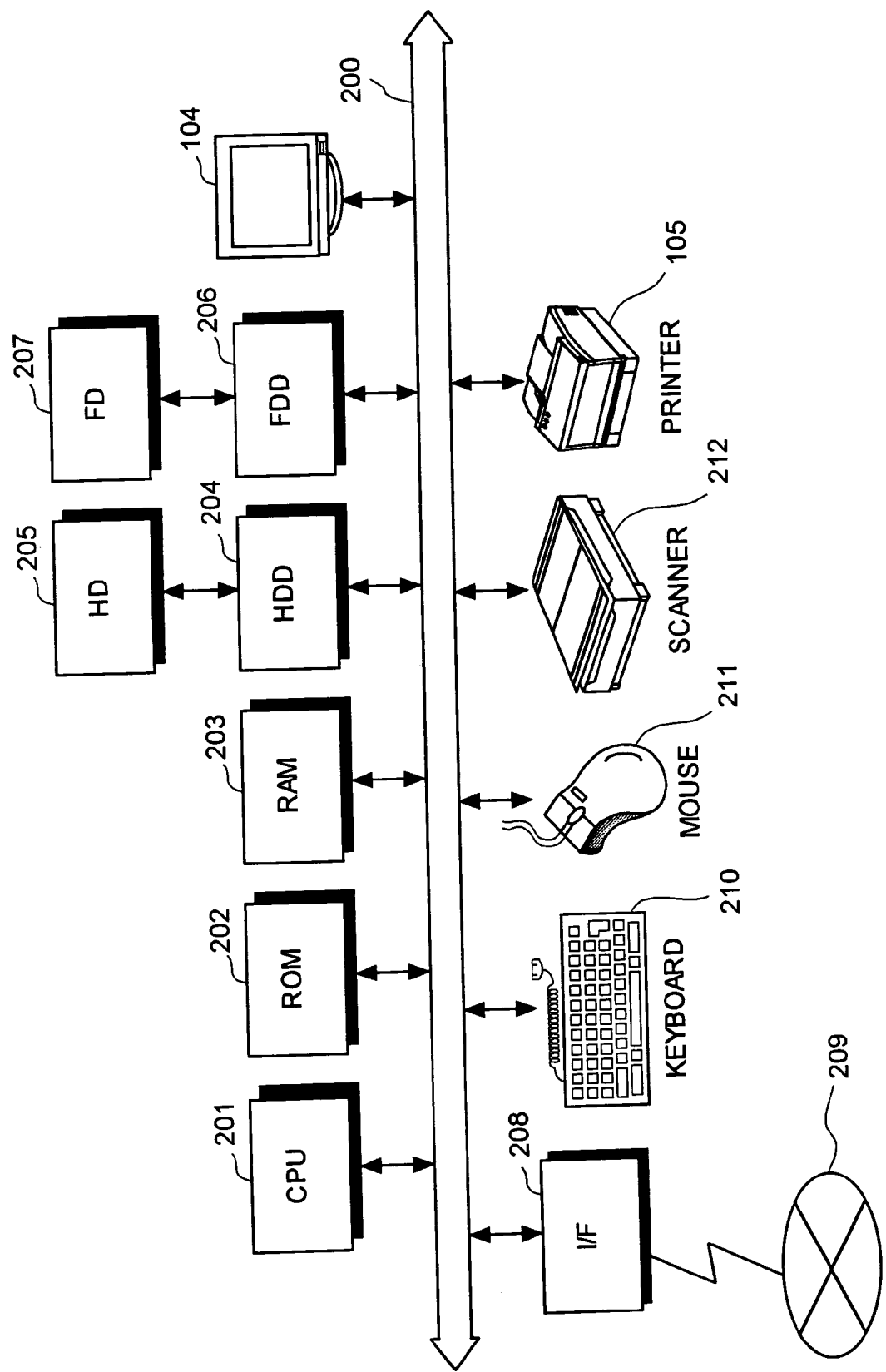
FIG. 2 is a block diagram of one example of a hardware configuration of an image storage PC and an image processing PC.

An image storage personal computer (PC) 102 and an image processing PC 103 are personal computers as examples of an information processing apparatus. The PCs can be servers or workstations. The image processing PC 103 is particularly preferably a supercomputer or the like having a high-rate processing ability. FIG. 2 is a block diagram for one example of a hardware configuration of the image storage PC 102 and the image processing PC 103. In FIG. 2, each of the image storage PC 102 and the image processing PC 103 includes a CPU 201, a ROM 202, a RAM 203, a HDD 204, a HD 205, a flexible disk drive (FDD) 206, a flexible disk (FD) 207 as one example of a detachable recording medium, an I/F (interface) 208, a keyboard 210, a mouse 211, and a scanner 212. A bus 200 connects the respective constituent elements to one another. Further, a monitor (display) 104 and a printer 105 are connected to the bus 200.

The CPU 201 controls the entire image analysis supporting device. The ROM 202 stores programs such as a boot program. The RAM 203 is employed as a work area for the CPU 201. The HDD 204 controls data to be read and written from and to the HD 205 under control of the CPU 201. The HD 205 stores data written under control of the HDD 204.

The FDD 206 controls data to be read and written from and to the FD 207 under control of the CPU 201. The FD 207 stores written data under control of the FDD 206, and causes the data recorded in the FD 207 to be read by the image processing apparatus. The detachable recording medium can be a CD-ROM (CD-R or CD-RW), a MO, a Digital Versatile Disk (DVD), a memory card, or the like in place of the FD 207. The monitor 104 displays such data as a document, an image, and function information as well as a cursor, an icon, and a tool box. The monitor 104 is, for example, a CRT, a TFT liquid crystal display, or a plasma display.

The I/F 208 is connected to a network 209 such as a LAN or the Internet through a communication line, and is connected to the other server or information processing apparatus through the network 209. The I/F 208 functions to interface the network with an interior of the image storage PC 102 or the image processing PC 103 and controls data to be input and output to and from the other server or an information terminal apparatus. The image storage PC 102 or the image processing PC 103 is connected to the other server or the information terminal apparatus through this I/F 208, such as a modem.

The keyboard 210 includes keys for inputting characters, numbers, various commands, and the like, and inputs data. The keyboard 210 can be replaced by a touch panel input pad, ten keys, or the like. The mouse 211 moves the cursor, selects a range, moves a window, changes a size, or the like. The mouse 211 can be replaced by such as a track ball and a joystick, as long as the element includes same functions as those of the mouse 211 as a pointing device.

The scanner 212 optically reads an image such as a driver image and fetches image data into the information processing apparatus. The scanner 212 also includes an OCR function that enables the scanner 212 to read printed information to be used as data. The printer 105, such as a laser printer or an inkjet printer, prints image data and character data.

Figure 3:
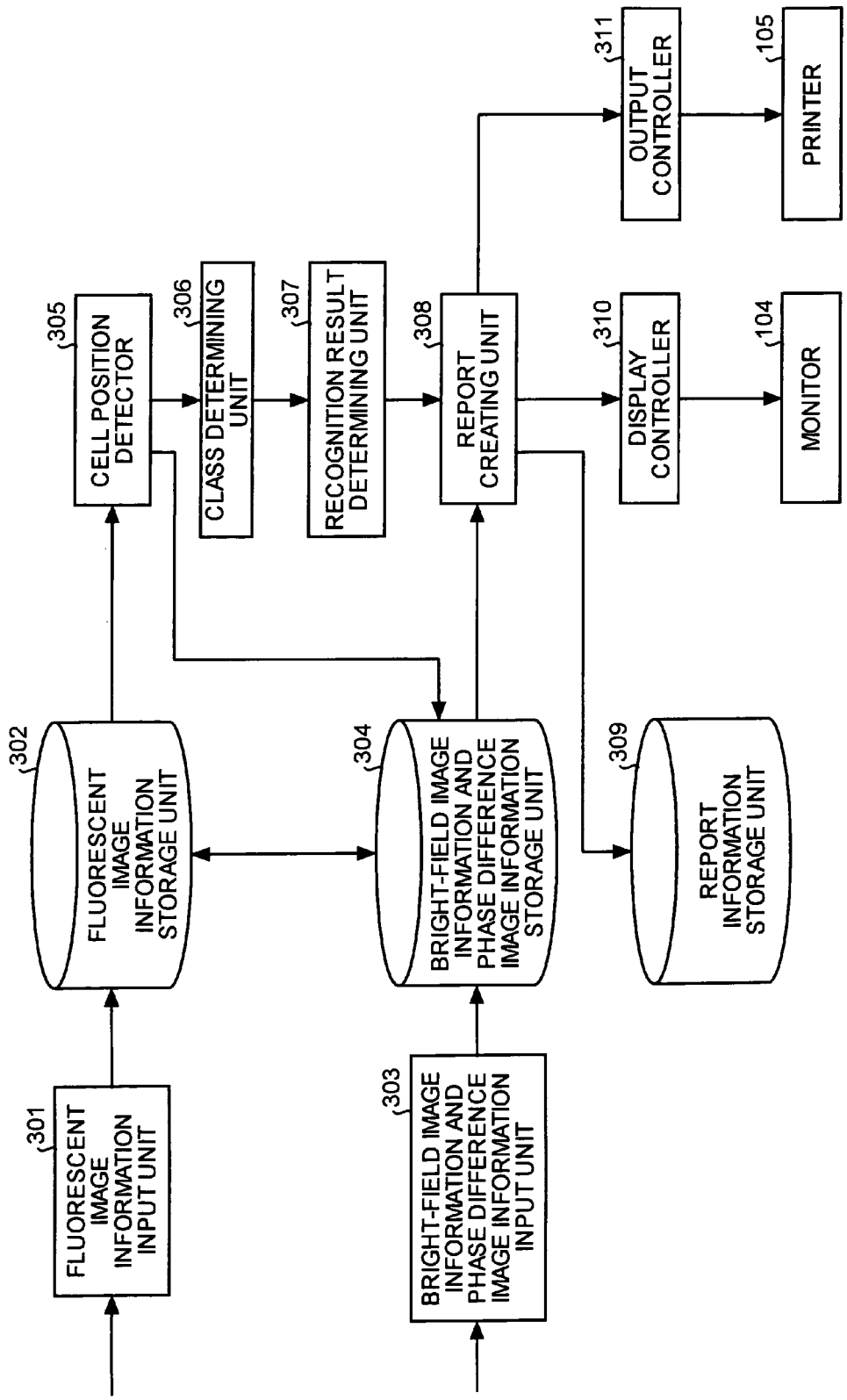
FIG. 3 is an explanatory view of a functional configuration of the image analysis supporting device.

FIG. 3 is a block diagram of one example of the functional configuration of the image analysis supporting device according to the embodiment of the present invention. In FIG. 3, the image analysis supporting device includes a fluorescent image information input unit 301, a fluorescent image information storage unit 302, a bright-field image information and phase difference image information input unit 303, a bright-field image information and phase difference image information storage unit 304, a cell position detector 305, a class determining unit 306, a recognition result determining unit 307, a report creating unit 308, a report information storage unit 309, a display controller 310, and an output controller 311.

The image storage PC 102 is functionally composed by the fluorescent image information input unit 301, the fluorescent image information storage unit 302, the bright-field image information and phase difference image information input unit 303, the bright-field image information and phase difference image information storage unit 304, and the report information storage unit 309. The image processing PC 103 is functionally composed by the cell position detector 305, the class determining unit 306, the recognition result determining unit 307, the report creating unit 308, the display controller 310, and the output controller 311. However, one PC can realize the both functions of the image storage PC 102 and the image processing PC 103.

The fluorescent image information input unit 301 accepts an input of fluorescent image information that is a photographed image of a plurality of cells adhering to a plurality of wells, to be explained later. The fluorescent image information storage unit 302 stores the florescent image information the input of which is accepted by the fluorescent image information input unit 301.

The bright-field image information and phase difference image information input unit 303 accepts an input of either the bright-field image information or the phase difference image information in the same field of view as that of the fluorescent image input by the fluorescent image information input unit 301. Alternatively, the bright-field image information and phase difference image information input unit 303 can accept the input of both of them. A selection of the bright-field image information or the phase difference image information to be input can be made according to a state of the cell to be photographed or the like. The bright-field image information and phase difference image information storage unit 304 stores the bright-field image information or the phase difference image information the input of which is accepted by the bright-field image information and phase difference image information input unit 303.

The cell position detector 305 detects a presence position of a cell in the fluorescent image on the basis of the fluorescent image information the input of which is accepted by the fluorescent image information input unit 301 and stored in the fluorescent image information storage unit 302. Namely, the cell position detector 305 compares a candidate region of a cell in the fluorescent image with either an average cell model or an average background model, and evaluates a similarity between them, thereby detecting the position of the cell in the fluorescent image. Specifically, the cell position detector 305 calculates a projection amount, that is, an inner product between a main component vector of at least either the average cell model or the average background model, and a feature vector of the candidate region, calculates an evaluation value by normalizing the calculated projection amount, and detects the position of the cell in the fluorescent image on the basis of the calculated evaluation value. The average cell model includes a main component vector, a distribution value, and an average value of each cell class in a sample image. Likewise, the average background model includes a main component vector, a distribution value, and an average value of a background class in the sample image. A detailed content of a cell position detection processing will be explained later.

The class determining unit 306 determines a class of the cell at the position detected by the cell position detector 305. The class determining unit 306 calculates a projection amount by obtaining an inner product between a main component vector of a model of each protein localization class, and a feature vector of the cell at the position detected by the cell position detector 305, calculates an evaluation value by normalizing the calculated projection amount, and determines the class of the cell on the basis of the calculated evaluation value. A detailed content of a class determination processing will be explained later.

The recognition result determining unit 307 determines a recognition result for each image or each well on the basis of the class determined by the class determining unit 306. A detailed content of a recognition result determination processing will be explained later.

Figure 18:
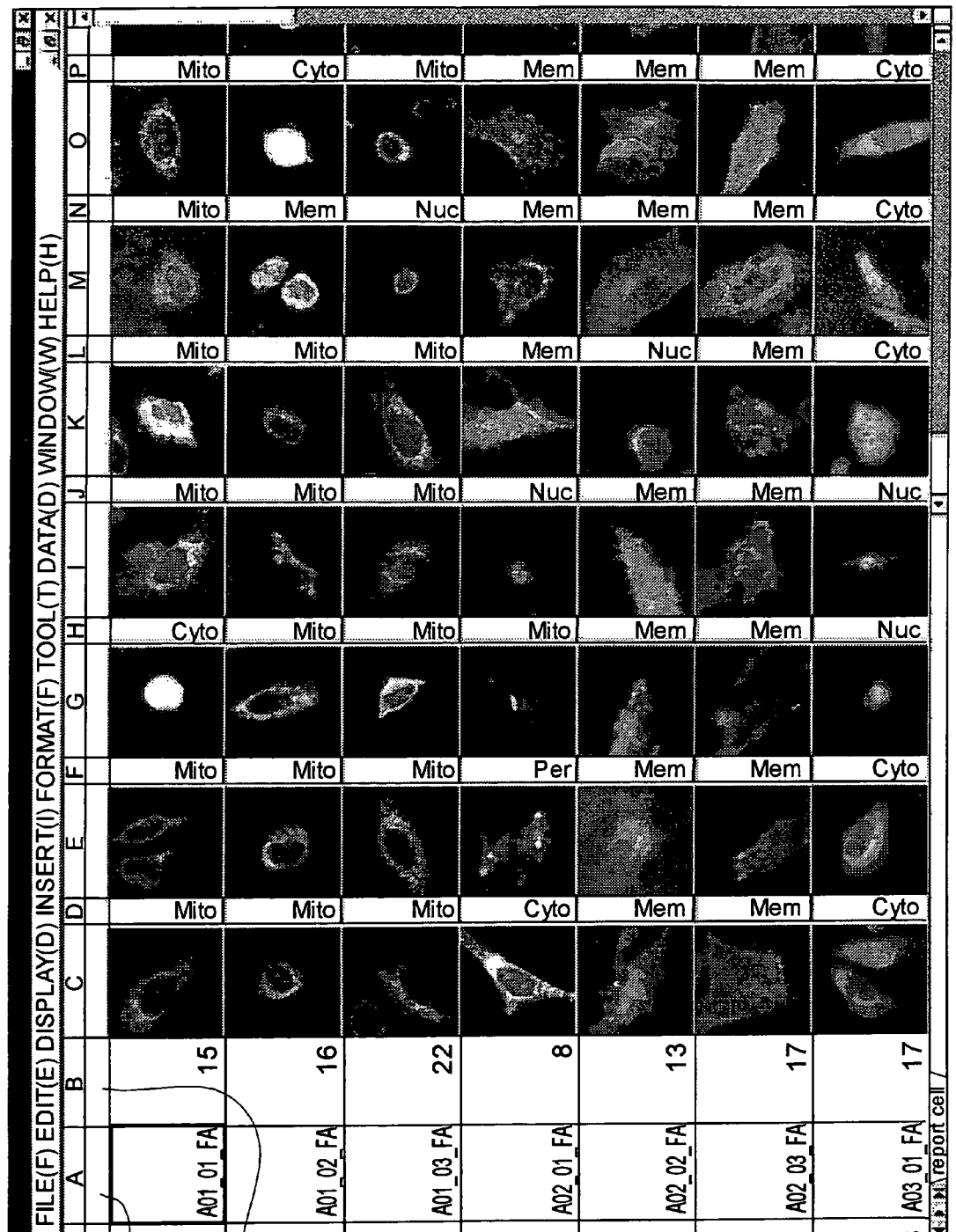
FIG. 18 is one example of a report screen.
Figure 19:
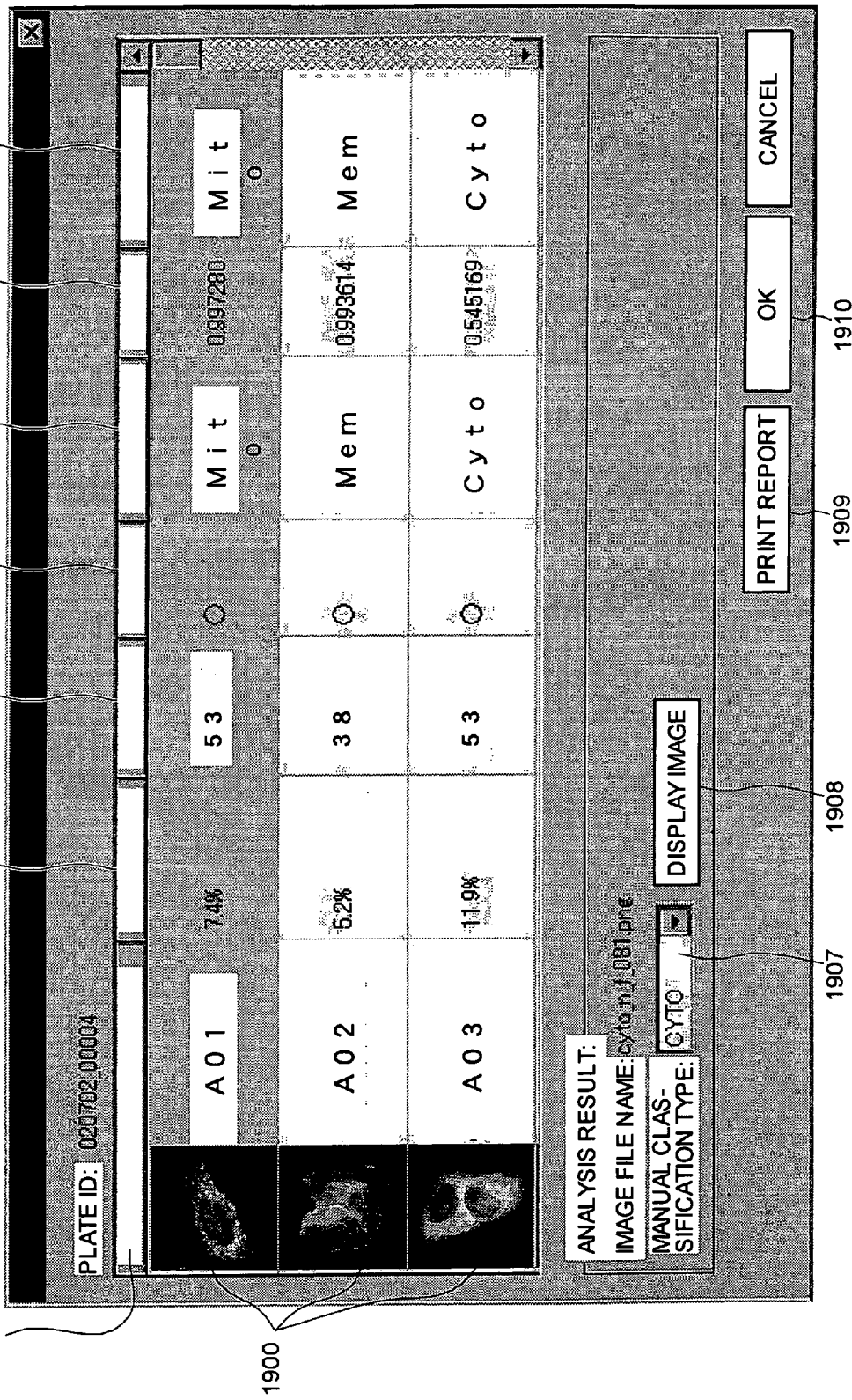
FIG. 19 is another example of the report screen.

The report creating unit 308 creates report information shown in FIG. 18 or 19, on the basis of information on the class determined by the class determining unit 306 and either the bright-field image information or the phase difference image information, the input of each of which is accepted by the bright-field image information and phase difference image information input unit 303 and which are stored in the bright-field image information and phase difference image information storage unit 304, of the cell extracted on the basis of the presence position detected by the cell position detector 305. The report creating unit 308 can create the report information including information on the recognition result determined by the recognition result determining unit 307. In addition, the report creating unit 308 can change the recognition result determined by the recognition result determining unit 307 when a command is input by an operator.

The report information storage unit 309 stores the report information created by the report creating unit 308. The display controller 310 controls the monitor 104 to display the report information created by the report creating unit 308 or stored in the report information storage unit 309. The output controller 311 controls the printer 105 to print the report information created by the report creating unit 308 or stored in the report information storage unit 309, or transmits the report information to the other information processing apparatus connected thereto through the network 209 by the I/F 208.

Functions of the fluorescent image information input unit 301 and the fluorescent image information storage unit 302 are specifically realized by one of or all of the keyboard 210, the mouse 211, the scanner 212, and the I/F 208. Functions of the cell position detector 305, the class determining unit 306, the recognition result determining unit 307, the report creating unit 308, the display controller 310, and the output controller 311 are specifically realized by making the CPU 201 execute a program stored in, for example, the ROM 202, the RAM 203, the HD 205, or the FD 207. Functions of the fluorescent image information storage unit 302, the bright-field image information and phase difference image information storage unit 304, and the report information storage unit 309 are specifically realized by, for example, the RAM 203, the HD 205 and the HDD 204, or the FD 207 and the FDD 206.

Figure 4:
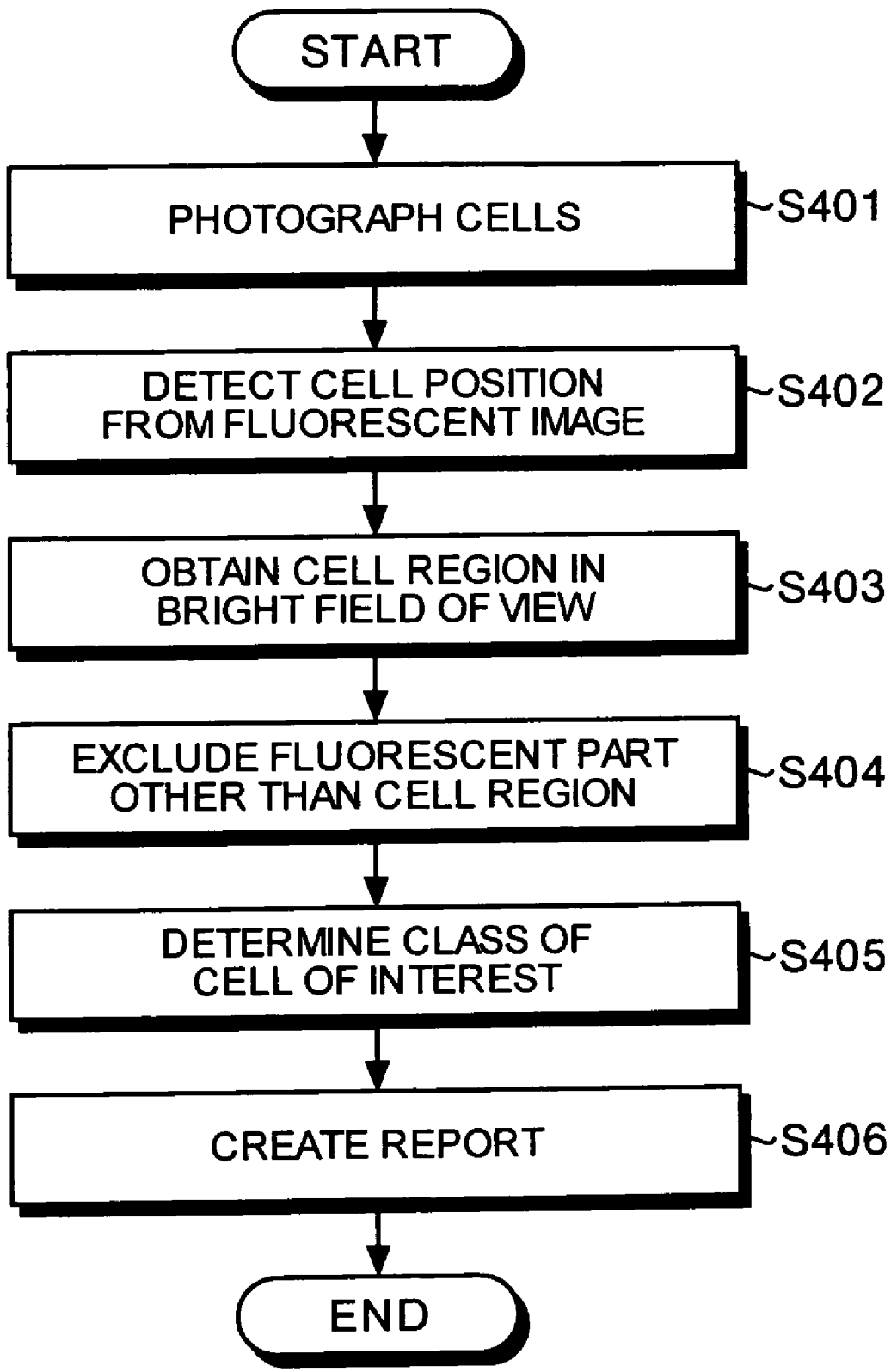
FIG. 4 is a flowchart of a processing performed by the image analysis supporting device.
Figure 5:
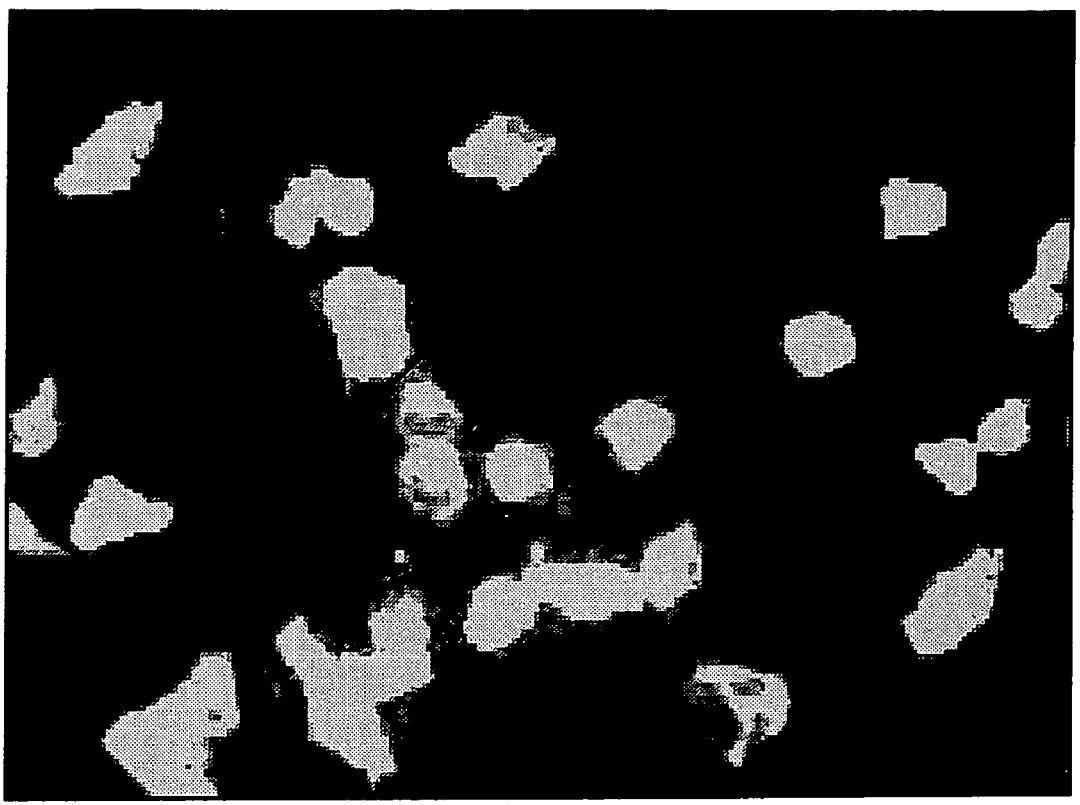
FIG. 5 is one example of a fluorescent image.

FIG. 4 is a flowchart of processing procedure performed by the image analysis supporting device according to the embodiment of the present invention. In the flowchart shown in FIG. 4, the apparatus photographs cells to acquire the fluorescent image and any one of the bright-field image and the phase difference image or both through procedures shown in FIG. 10, to be explained later (step S401). FIG. 5 depicts one example of the fluorescent image. In the fluorescent image, a fluorescent marker is applied to each cDNA, and a gene expression cell can be specified by the fluorescent marker emitting a light in a cell. Even if the cDNAs are injected, they do not enter all cells. As shown in FIG. 5, only nuclei of cells, into each of which the cDNA is successfully injected, emits a light.

Figure 6:
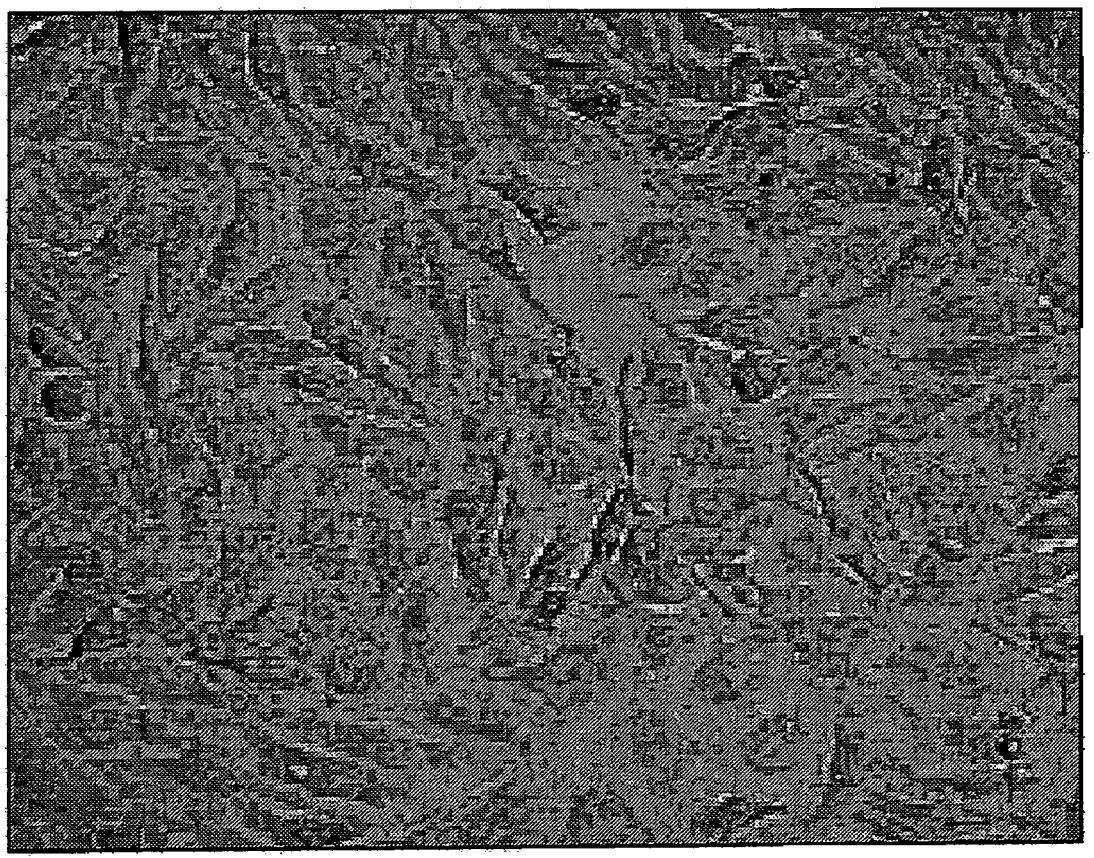
FIG. 6 is one example of a bright-field image.
Figure 7:
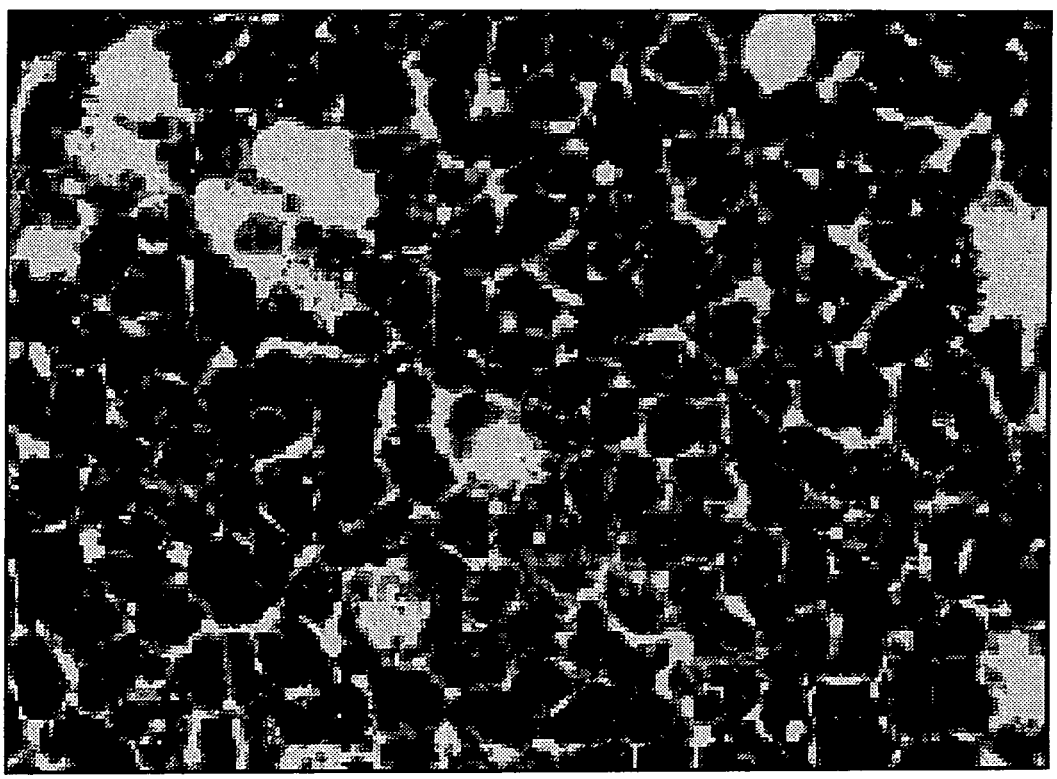
FIG. 7 is one example of a phase difference image.

FIG. 6 depicts one example of the bright-field image. The bright-field image is photographed using an ordinary lens, and enables recognizing a shape (profile) of a cell. FIG. 7 depicts one example of the phase difference image. The phase difference image is photographed using a refractive index of a lens, and enables recognizing even a content of the cell. The bright-field image has an advantage in that focusing can be easily performed, while the phase difference field has an advantage in that the profile of the cell can be displayed more clearly than the bright-field image although it takes longer time to perform focusing. Whether one of the bright-field image or the phase difference image is used or the both are used simultaneously can be appropriately selected according to experimental and analysis conditions. For example, the following method is considered. After performing focusing using a bright-field image, a fluorescent image is photographed. The lens is changed to another lens in an in-focus state, a phase difference image is photographed, and only the fluorescent image and the phase difference image are stored in the image storage PC 102.

Figure 11:
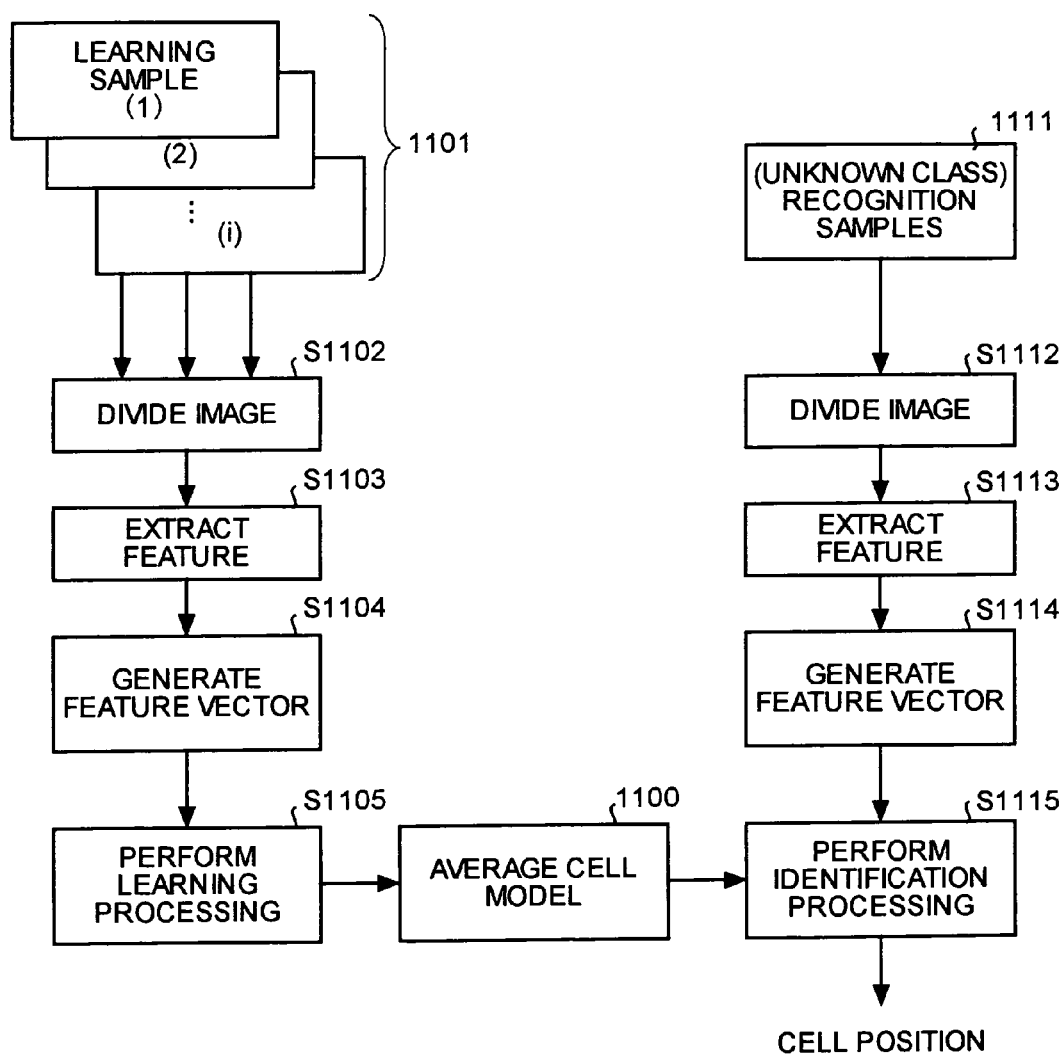
FIG. 11 is an explanatory view of a content of a cell position detection processing.

A position of a cell is detected from the fluorescent image acquired at step S401 (recognition samples (unknown class) 1111 shown in FIG. 11) (step S402). Using the bright-field image or phase difference image acquired at step S401, a cell region of the cell, the position of which is detected at step S402 is obtained in a bright field of view (step S403). A fluorescent part other than the cell region is thereby excluded (step S404). A class of each cell specified by the cell region left after excluding the other fluorescent part (step S404) is determined, thereby determining a class of each cell (step S405). A report is created on the basis of the result (step S406), thus finishing a series of processing procedures.

Figure 8:
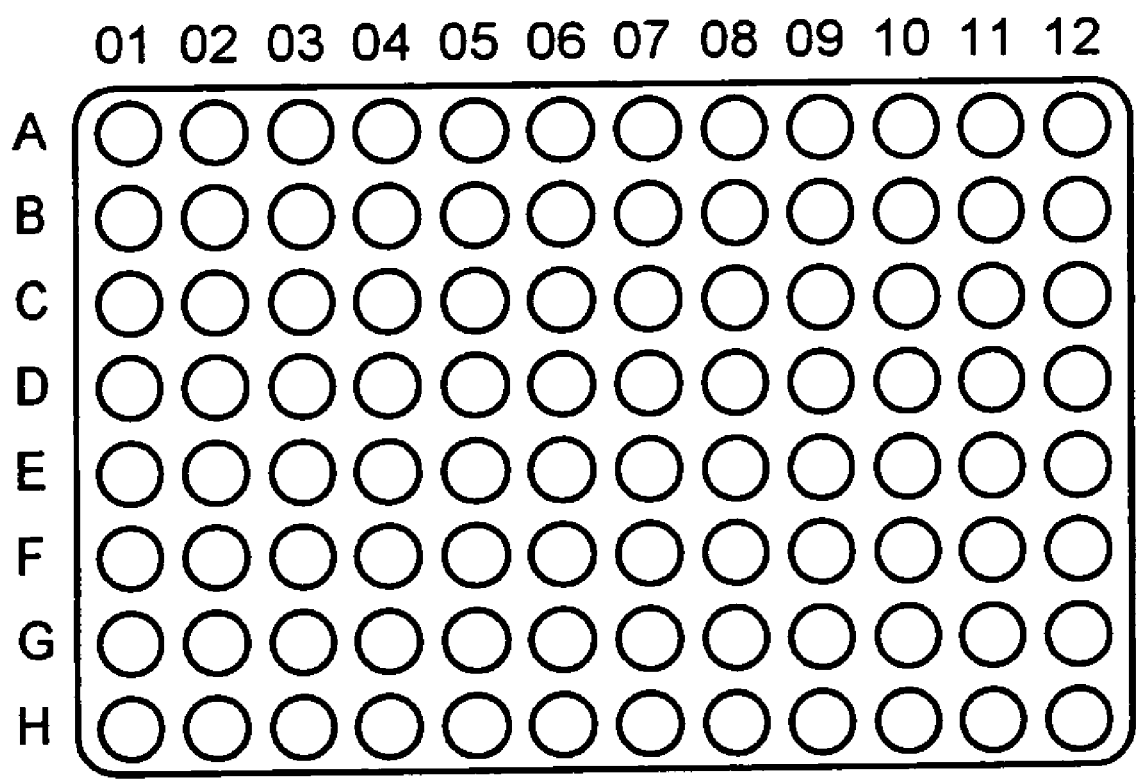
FIG. 8 is an explanatory view of one example of a plate for cell cultivation.

FIG. 8 is an explanatory view of one example of a 96-well plate for cell cultivation. In FIG. 8, the 96-well plate has wells arranged in a lattice fashion. Each well is allocated one of symbols A to H for a longitudinal direction and one of numbers 01 to 12 for a lateral direction. For example, an uppermost left well is allocated "A01", and a lowermost right well is allocated "H12". Accordingly, one plate has 8×12=96 wells of "A01 to A12", "B01 to B12", . . . , and "H01 to H12".

Figure 9:
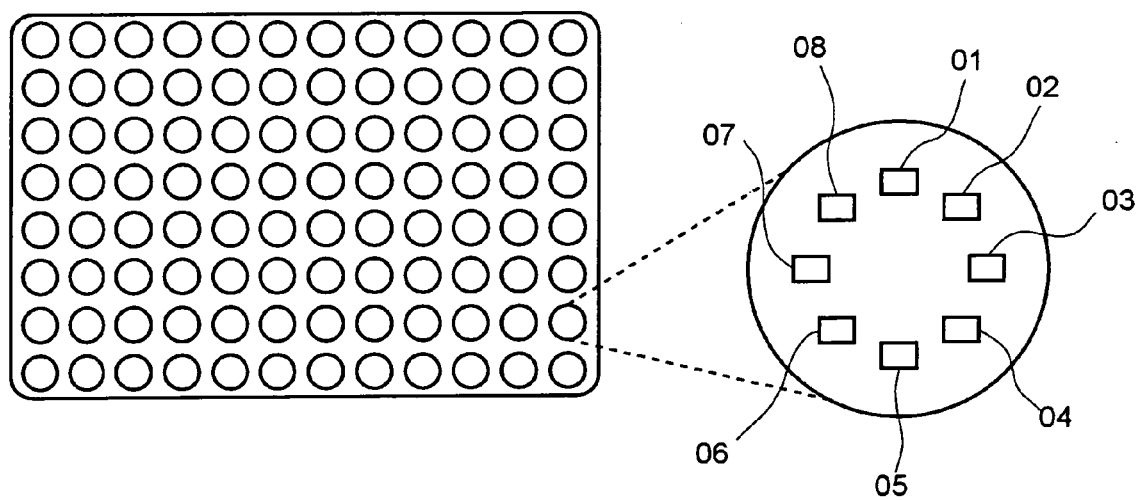
FIG. 9 is an explanatory view of one example of a photographic region when a plurality of images is obtained from one well.

FIG. 9 is an explanatory view that depicts one example of a photographic region when a plurality of images is obtained from one well, which is an enlargement of one well ("G12 well") on the well plate. In FIG. 9, for the G12 well, fluorescent images, bright-field images, and phase difference images are acquired at a plurality of positions (01 to 08), respectively. During the photographing, positions are concentrically changed, that is, the images are photographed in the order of 01→02→ . . . →08. Alternatively, the images can be acquired with the positions changed not concentrically but spirally.

Figure 10:
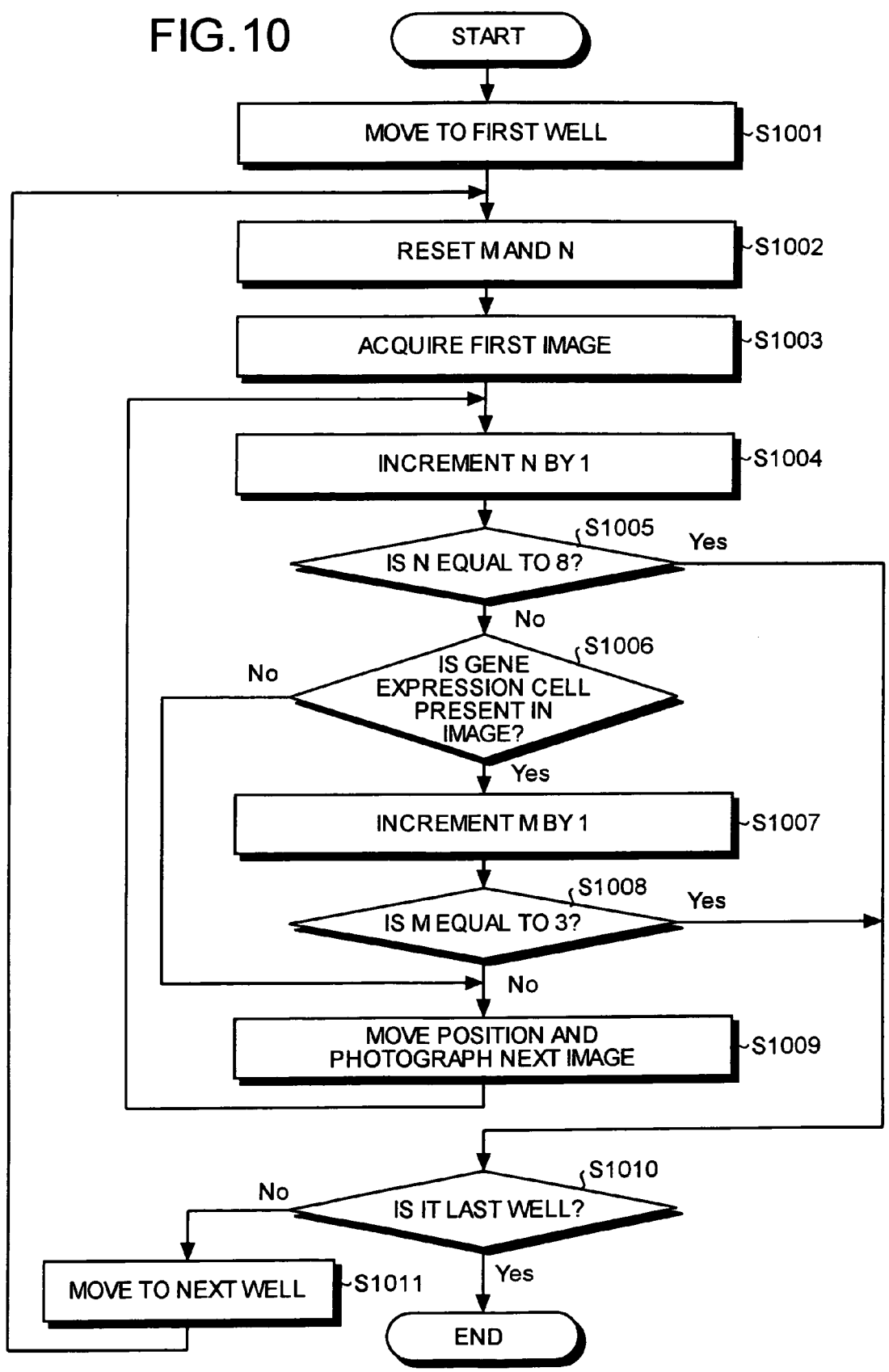
FIG. 10 is a flowchart of an image acquisition processing.

FIG. 10 is a flowchart of an image acquisition processing using the 96-well plate. In FIG. 10, a focusing target is moved to a first well (A01), and the first well is made into a photographable state (step S1001). An M counter and an N counter are reset (step S1002). The first image (the fluorescent image) is acquired by photographing the cell's in the first well (step S1003), and the N counter is incremented by one (step S1004).

It is determined whether the N counter reaches a preset value, for example, "8" (step S1005). If the N counter does not reach "8" yet ("No" at step S1005), it is determined whether a gene expression cell is present in the image acquired at step S1003 (step S1006). Whether a gene expression cell is present can be determined by depending on, for example, whether a fluorescent part is present on the fluorescent image. If it is determined that the gene expression cell is present ("Yes" at step S1006), then one of or both of the bright-field image and the phase difference image in the same field of view are acquired, and the M counter is incremented by one (step S1007). If it is determined that no gene expression cell is present ("No" at step S1006), nothing is performed and the processing proceeds to step S1009.

It is determined whether the M counter reaches a preset value, for example, "3" (step S1008). If the M counter does not reach "3" yet ("No" at step S1008), images are acquired at a next position (step S1009). Thereafter, the processing returns to step S1004 and the respective processing procedures at the steps S1004 to S1009 are repeatedly performed. If it is determined that the N counter reaches "8" at step S1005 ("Yes" at step S1005) or if it is determined that the M counter reaches "3" at step S1008 ("Yes" at step S1008), the processing proceeds to step S1010.

At step S1010, it is determined whether the present well is a last well. If the present well is not the last well ("No" at step S1010), the focusing target is moved to a next well (step S1011), and the processing returns to step S1002. For the next well, the processing procedures at the respective steps S1002 to S1009 are repeatedly performed. If it is determined at step S1010 that the present well is the last well ("Yes" at step S1010), a series of processing procedures are finished.

When three sets of images including the gene expression cell are acquired for each well by these processing procedures, further photographing is stopped. This makes it possible to suppress acquiring unnecessary images, and to save a processing time, a storage capacity, and the like. Even if an image of the gene expression cell cannot be acquired, up to eight images are acquired and the focusing target is moved to the next well. It is noted that settings of the M counter and the N counter can be appropriately changed.

FIG. 11 is an explanatory view of a content of a cell position detection processing. In FIG. 11, learning samples 1101 in large quantities prepared in advance are input. The learning samples 1101 include both a background learning image and a cell learning image. Each of the samples is divided (step S1102), a feature is extracted from the divided samples (step S1103), and the extracted feature is normalized to generate a feature vector (step S1104). Further, a learning processing is performed using the generated feature vector (step S1105), thereby creating an average cell model 1100.

Meanwhile, the cells in the fluorescent images of recognition samples 1111 are class-unknown cells, in other words, classes of the cells are not determined yet. The recognition samples 1111 are input in the same procedures as those for the learning samples 1101. Each of the samples is divided (step S1112), a feature is extracted from the divided samples (step S1113), and the extracted feature is normalized, thereby creating a feature vector (step S1114). Using the average cell model 1100, an identification processing is performed (step S1115), thus extracting the position of the cell in each of the fluorescent images.

Figure 12:
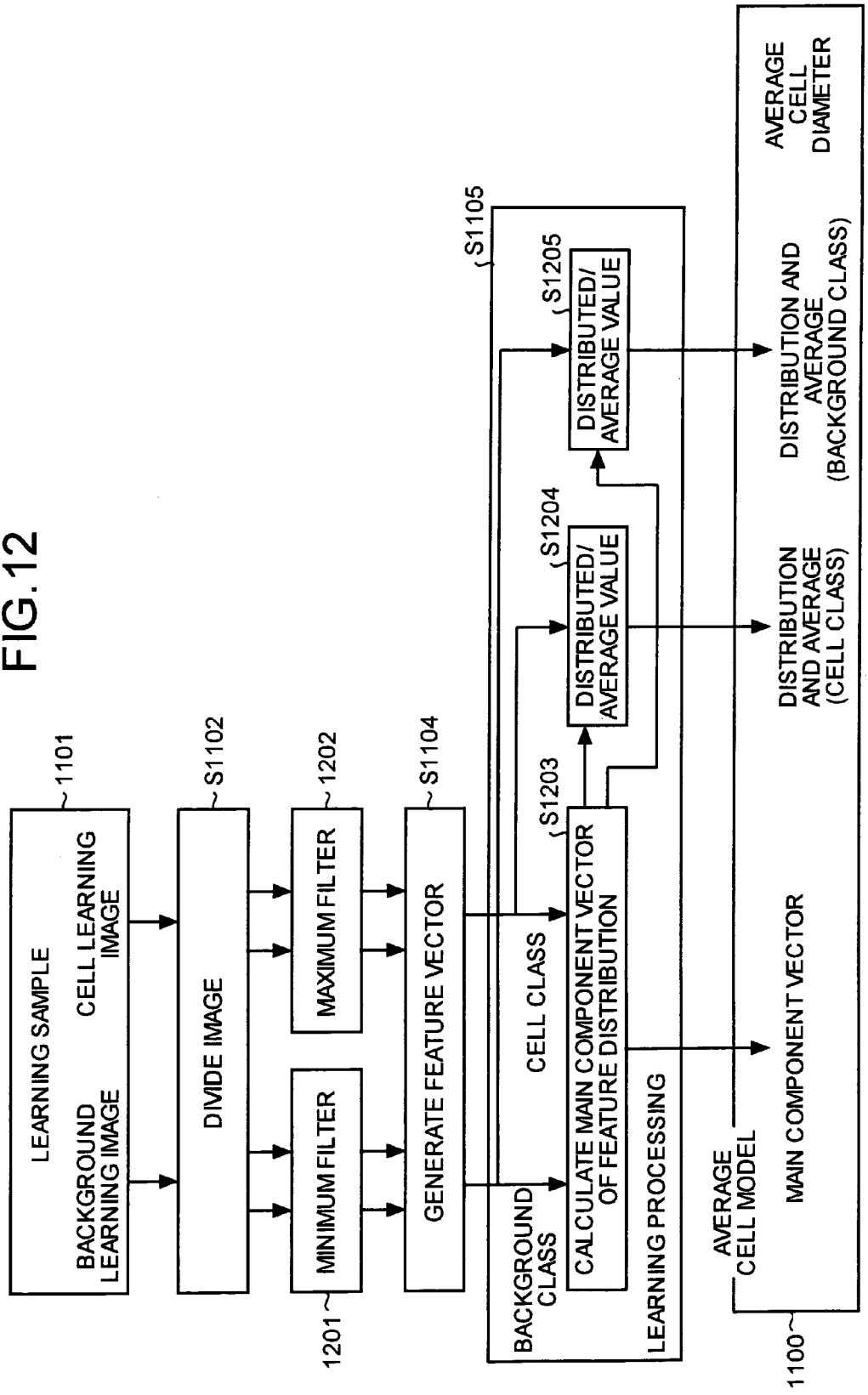
FIG. 12 is another explanatory view of the content of the cell position detection processing.

FIG. 12 is an explanatory view of the content of the cell position detection processing, and specifically, FIG. 12 depicts an average cell model generation processing. In FIG. 12, each of the target learning samples 1101 is divided into a preset number of segments (step S1102). If each of the learning samples 1101 is divided into, for example, 4*4 pixel regions, the divided learning sample (original image) 1101 is processed, as a preprocessing, using a maximum filter 1202 for replacing a maximum value of the 4*4 pixels by one pixel, and a minimum filter 1201 for replacing a minimum value of the 4*4 pixels by one pixel. By doing so, the learning sample 1101 is compressed to a maxim image and a minimum image at a size of 1/4*1/4. 96*96 pixel regions of the original image can be thereby represented by a 1152-dimensional feature vector having n=24*24 (=1152) density values as a feature amount.

The feature vector of the learning sample j, which is normalized (that is, an average value is 0 and a distribution value is 1 among the respective feature amounts of all the samples) for creating the average cell model, is assumed as $x_j=(x_{j,0}, x_{j,1}, x_{j,2}, \ldots, x_{j,1151})$. The feature vector is thus generated (step S1104).

Further, a covariance matrix R of all the learning samples is assumed to be represented by:

$$R = E_j(x_j \cdot x_j^T).$$

An eigenvalue problem of this matrix, as represented by:

$$R\phi_k \lambda_k \phi_k,$$

is solved, thereby calculating an eigenvector $\phi_k$ (where $1 < k \leq n$) and an eigenvalue $\lambda_k$ (where $\lambda_k > \lambda_{k+1}$) (step S1203). An eigenvector $\phi_1$ for a maximum eigenvalue $\lambda_1$ is a first main component (main component vector).

If it is assumed that an average vector of a cell class (number of samples: $m_1$) is $m^{(c)}$ and that of a background class (number of samples: $m_2$) is $m^{(b)}$, then a projection of a learning sample $x^{(c)}$ in the cell class on the first main component is represented by $^1x^{(c)} = \{x^{(c)T}\phi_1\}$, and a projection of the average vector $m^{(c)}$ on the first main component is represented by $^1m^{(c)} = \{m^{(c)T}\phi_1\}$.

A distribution value of projections of all the learning samples in the cell class is represented by $$\sigma^{(c)2} = \frac{1}{m_1} \sum_{i=1}^{m_1} (^1x_i^{(c)} - {}^1m^{(c)})^2$$

(step S1204), and a distribution value of projections of all the learning samples in the background class is equal to that in the cell class (step S1205).

Figure 13:
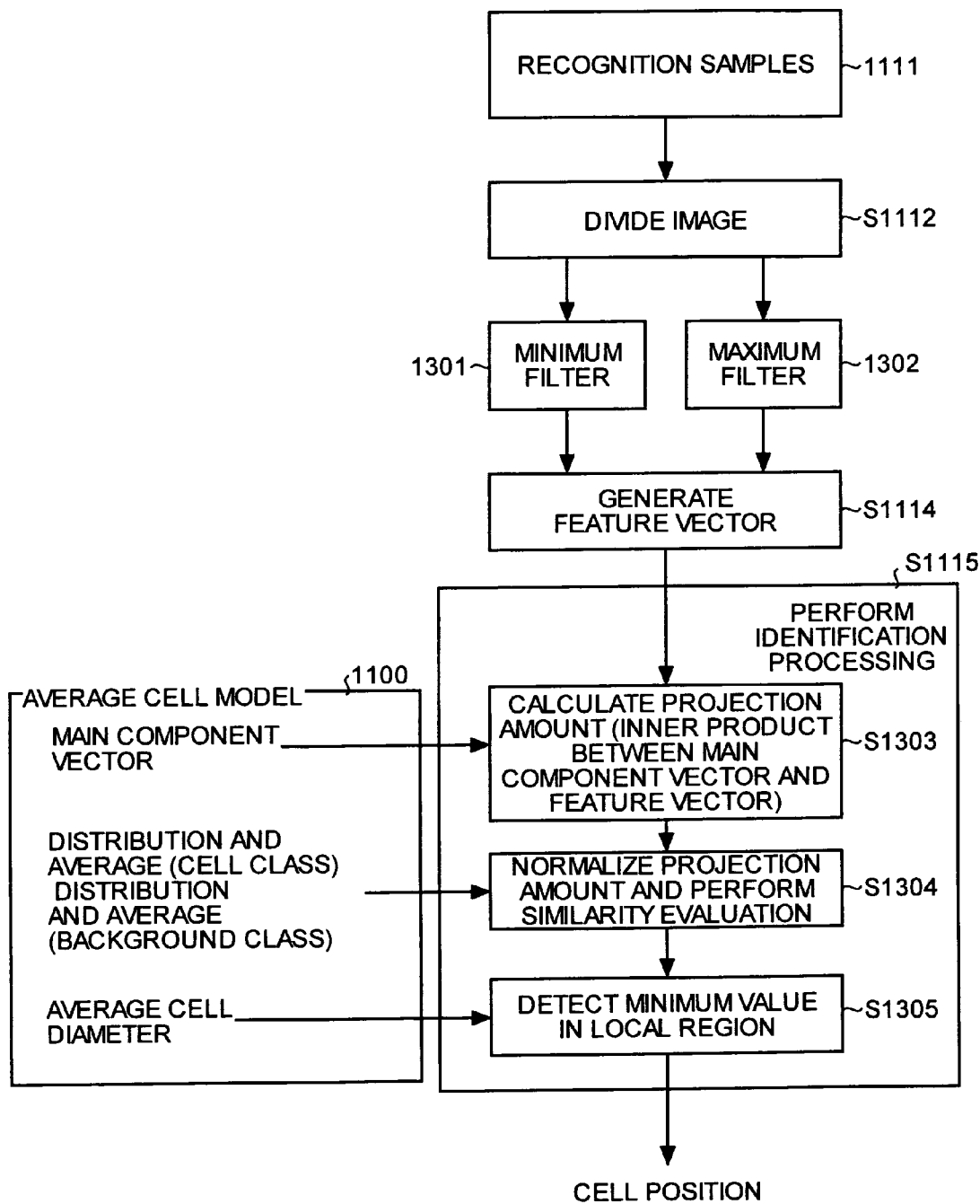
FIG. 13 is still another explanatory view of the content of the cell position detection processing.

FIG. 13 is an explanatory view of the content of the cell position detection processing. Specifically, FIG. 13 depicts an average cell model generation processing. In FIG. 13, the target recognition samples 1111 are divided into a preset number of segments similarly to the learning samples 1101 (step S1112). Each of the divided recognition samples 1111 is processed, as a preprocessing, using a maximum filter 1302 for replacing the 4*4 pixels by one pixel of a maximum value of them and a minimum filter 1301 for replacing the 4*4 pixels by one pixel of a minimum value of them. By doing so, the recognition samples 1111 are compressed to a maxim image and a minimum image at a size of 1/4*1/4. 96*96 pixel regions of the recognition sample 1111 can be represented by a 1152-dimensional feature vector having n=24*24 (=1152) density values as a feature amount.

The feature vector of the learning sample j, which is normalized (that is, an average value is 0 and a distribution value is 1 among the respective feature amounts of all the samples) for creating the average cell model, is assumed as $x_j=(x_{j,0}, x_{j,1}, x_{j,2}, \ldots, x_{j,1151})$. The feature vector is thus generated (step S1114). The procedures executed so far are similar to those for the processing on the learning samples 1101.

Regarding a point of a coordinate (i, j) of an image subjected to the preprocessing, if a feature vector of a 24*24 pixel region around this point that serves as a central point is xi,j, a projection (amount) of projecting the feature vector xi,j on the first main component (main component vector) is calculated (step S1303). The calculated projection (amount) is normalized and a similarity evaluation is performed. Namely, a value obtained by dividing a length between the projection (amount) and a projection 1m(c) of the average vector m(c) in the cell class by a distribution σ(c)2 of the cell class is set as an evaluation value of the cell class at the coordinate point (i, j) (step S1304).

If the following relationship is satisfied, it is determined that the point on the coordinate (i, j) belongs to the cell class.

$$\{(X_{i,j}^T\phi_1 - {}^1m^{(b)})^2/\sigma^{(b)2} > \{X_{i,j}^T\phi_1 - {}^1m^{(c)}\}^2/\sigma^{(c)2}$$

Figure 14:
FIG. 14 is an explanatory view of one example of cell positions detected.

A minimum value in a local region is detected on the basis of a preset average cell diameter (step S1305). As a result, the cell position is detected. The cell positions specified on the fluorescent image are shown in FIG. 14. In FIG. 14, each position with "+" is the cell position.

Figure 15:
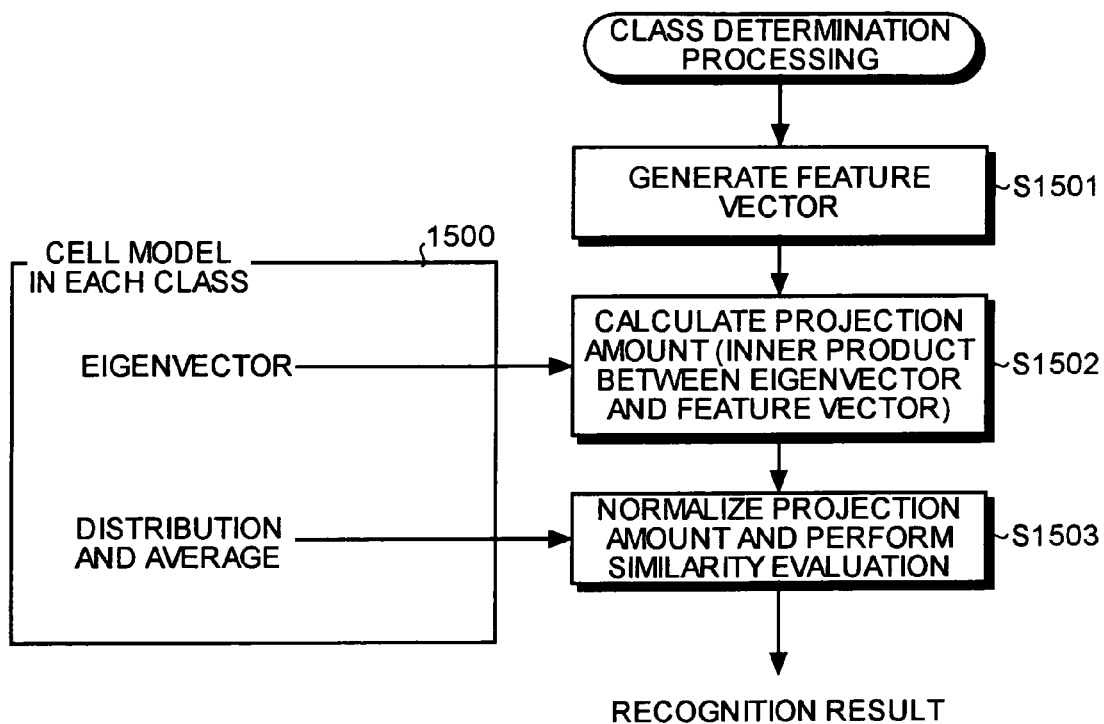
FIG. 15 is an explanatory view of a content of a class determination processing.

FIG. 15 is an explanatory view of an example of a class determination processing. In FIG. 15, reference sign 1500 denotes each class, that is, a protein localization cell model, which is composed by average cell model information on each class. Types of the protein localization cell model are, for example those shown in FIG. 20. A cell model generating method is the same as the average cell model generating method.

As processing procedures, a feature vector of a class determination target recognition sample is generated (step S1501). The feature vector is generated using all of or a part of various feature amounts, for example, those related to density statistics, those related to edge element features, those related to shape features, those related to texture features, and those related to run-length statistics.

Among the feature amounts, those related to density statistics specifically include a luminance average of all the images, a luminance distribution of all the images, an overall distribution of averages in non-background rectangular blocks, an overall average of distributions in the non-background rectangular blocks, a luminance average of secondary differential images, a luminance distribution of the secondary differential images, an overall average of averages in the non-background rectangular blocks, and the like.

Those related to edge element features specifically include an average of neighborhood density differences, a distribution of the neighborhood density differences, a luminance average of phase difference edge images, a lateral dark part run-length average of the phase difference edge images, a lateral bright part run-length average of the phase difference edge images, a longitudinal dark part run-length average of the phase difference edge images, a longitudinal bright part run-length average of the phase difference edge images, a covariance of a density cooccurrence matrix of the phase difference edge images, a horizontal standard deviation of the density cooccurrence matrix of the phase difference edge images, a vertical standard deviation of the density cooccurrence matrix of the phase difference edge images, a sample correlation coefficient of the density cooccurrence matrix of the phase difference edge images, a ratio of the horizontal standard deviation to the vertical standard deviation of the density cooccurrence matrix of the phase difference edge images, and the like.

Those related to shape features specifically include the number of labels, a sum of areas of labeling items, a sum of circumferential lengths of the labeling items, an average luminance ratio of all images to a non-background part, an average area of the labeling items, an average circumferential length of the labeling items, an average circularity of the labeling items, an average complexity of the labeling items, and the like.

Those related to texture features include a horizontal average of density cooccurrence matrixes, a vertical average of the density cooccurrence matrixes, a contrast of the density cooccurrence matrixes, a covariance of the density cooccurrence matrixes, a horizontal standard deviation of the density cooccurrence matrixes, a vertical standard deviation of the density cooccurrence matrixes, a power of the density cooccurrence matrixes, a sample correlation coefficient of the density cooccurrence matrixes, a ratio of the horizontal average to the vertical average of the density cooccurrence matrixes, and the like.

Those related to run-length statistics include longitudinal and lateral dark part run-length averages, longitudinal and lateral bright part run-length averages, a ratio of the dark part run-length average to the bright part run-length average, and the like.

Figure 16:
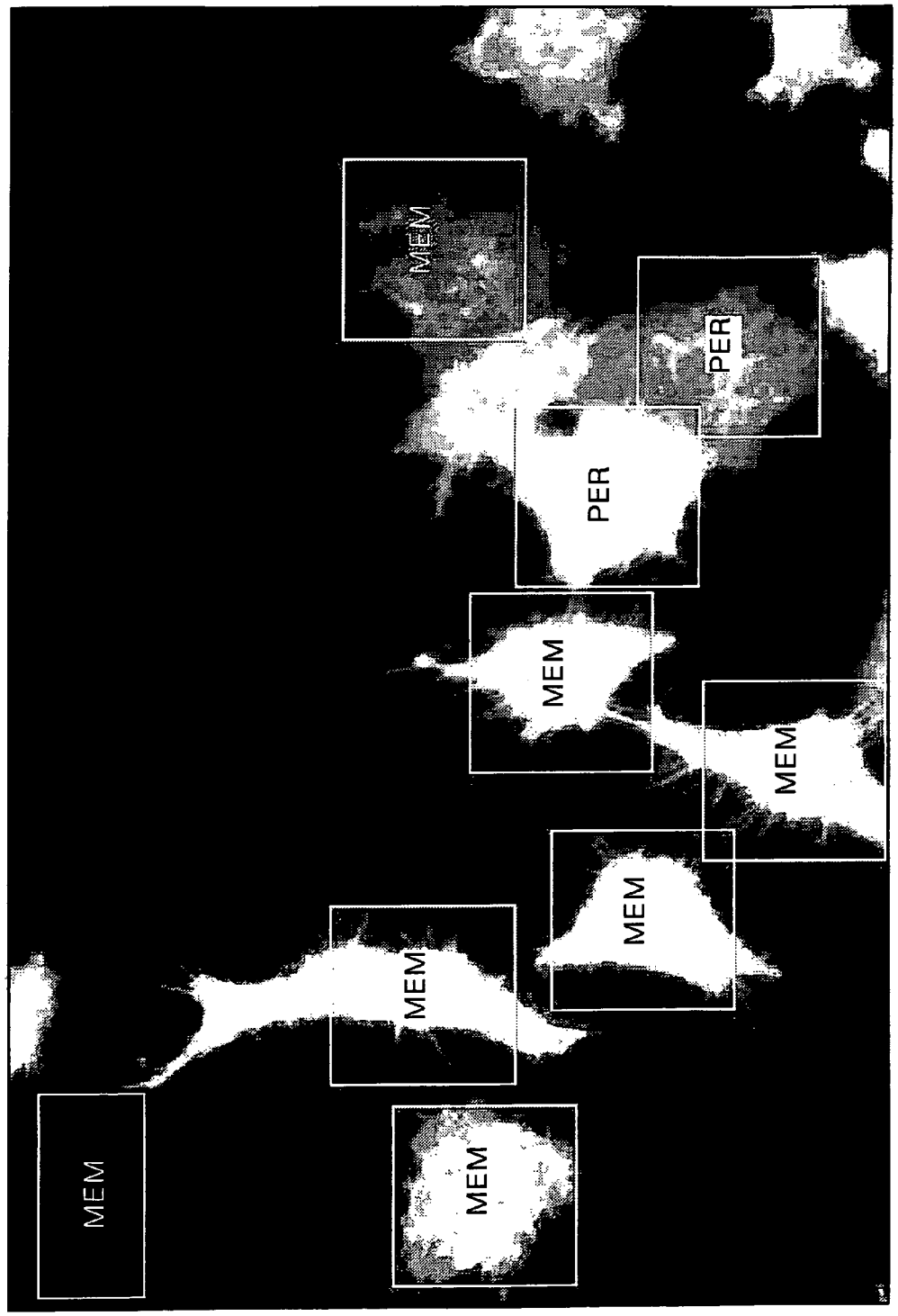
FIG. 16 is an explanatory view of one example of a result of the class determination processing.

An inner product between an eigenvector of the cell model 1500 in each class and the feature vector generated at step S1501 is obtained, thereby calculating a projection amount (step S1502). The calculated projection amount is normalized using distribution and average values, thereby performing a similarity evaluation (step S1503). Since these processing procedures are the same as those at the steps S1303 and S1304 shown in FIG. 13, they will not be explained herein in detail. Higher n (where n is a natural number) eigenvectors are used instead of the main component vector so as to realize a better classification of the learning patterns. As a result of the similarity evaluation, a recognition result is obtained. The recognition result is a result regarding to which of the protein localization classes, the each class determination target recognition sample belongs. Once it is determined which of the classes the each class determination target recognition sample cell belongs, the cell classification is performed. FIG. 16 depicts that classes, which are recognition results of the respective cells the positions of which are specified on the fluorescent image, are displayed in abbreviations. In FIG. 16, "MEM" indicates that this cell is a membrane.

Figure 17:
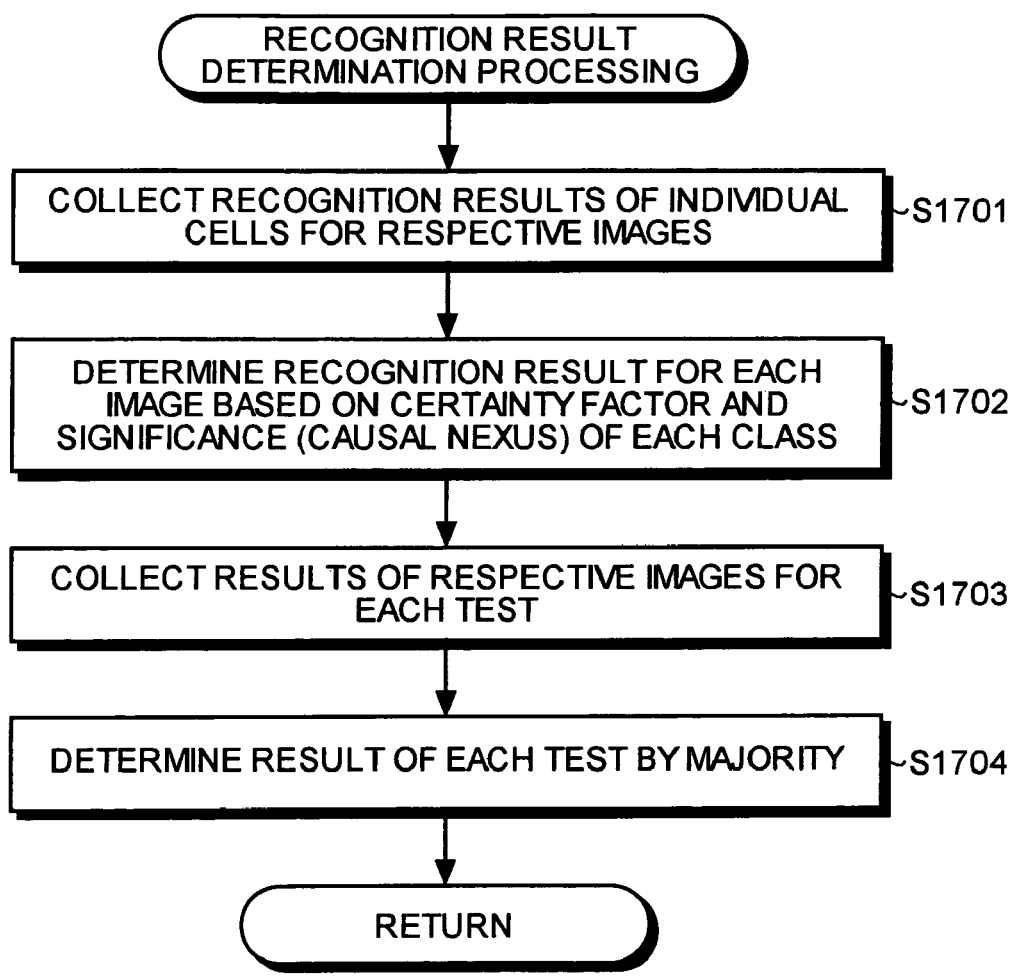
FIG. 17 is a flowchart of a recognition result determination processing.

FIG. 17 is a flowchart of a recognition result determination processing. The recognition result determination processing is intended to determine recognition results for respective images or respective tests from the individual cell recognition results. In the flowchart shown in FIG. 17, the recognition results for the respective cells are collected for the respective images (step S1701). The collected recognition result for each cell is determined in view of a certainty factor acquired from a recognition algorithm and significance (causal nexus) of each class (step S1702).

For example, it is assumed that four types of classes A, B, C, and D are present and that certainty factor thresholds of the respective classes are TA, TB, TC, and TD. It is also assumed that the certainty factors of the respective classes are obtained as xA, xB, xC, and xD. It is further assumed that a dependency relationship is held among the classes B, C, and D, i.e., the classes are changed with passage of time from B to C and from C to D (B→C→D). Based on these assumptions, if each certainty factor is smaller than the corresponding certainty factor threshold, an unknown pattern is output as the recognition result. If the certainty factors of the classes A and B are equal to or greater than the corresponding certainty factor thresholds, the class having the greater certainty factor is output as the result. If the certainty factors of the classes B, C, and D are all equal to or greater than the certainty factor thresholds, the class B based on which the dependency relationship is held is output as the result.

If the above content of the processing is applied to an example of protein localization patterns, a localization to endoplasmic reticulum is changed to a localization to Golgi and to a localization to membrane with the passage of time. Therefore, the localization to endoplasmic reticulum, the localization to Golgi, and the localization to membrane correspond to the classes B, C, and D, respectively. A localization to mitochondria, for example, corresponds to the class A.

In this way, the results for the respective images are collected for the respective tests (step S1703). The result for the respective tests is decided by majority (step S1704), thus finishing a series of processing procedures. As explained so far, using a foresight that single solution is included per image or per test, the recognition results (gene functions) for the respective images or respective tests can be estimated.

FIGS. 18 and 19 are explanatory views for examples of the report screen. FIG. 20 depicts an example of an intracellular protein localization image, and depicts a list of class names and class abbreviations corresponding to the respective image examples. FIG. 18 depicts a report screen created based on the recognition results obtained by the class determination processing explained with reference to FIG. 15. "A01 01 FA" in "Field-of-view image" box indicates a well "A01" and a photographic position "01", and also indicates that 15 gene expression cells are present on this fluorescent image. Further, bright-field images and phase difference images cut out of this field-of-view image are attached and abbreviations of determined classes are displayed.

FIG. 19 depicts a report screen created based on the result obtained by the recognition result determination processing explained with reference to FIG. 17. Reference sign 1900 denotes a representative image for each well. A list of items, i.e., an item "fluorescent part ratio" 1901 that indicates a ratio of a fluorescent part to all fluorescent images photographed for one well, an item "number of cells" 1902 of the all fluorescent images photographed for one well, an item "exposure state" 1903, an item "automatic class type" 1904 that indicates a class acquired by the recognition result determination processing, an item "similarity" 1905 with the model, and an item "manual class type" 1906 are displayed. Each of the items 1901 to 1906 can be displayed by sorting.

By changing an item of a manual class type display box 1907, the "manual class type" can be changed. By doing so, if a visual recognition result differs from the automatically determined recognition result, a content of one of the results determined to be correct can be easily selected. In addition, by depressing an image display button 1908, each representative image can be changed to a desired image. By depressing a "print report" button 1909, a content which is currently displayed is printed. By depressing an "OK" button 1910, the content is confirmed as displayed and stored in the report information storage unit 309. It is also possible to read the already stored report from the report information storage unit 309, change a content of the report thus read, and store the report again in the report information storage unit 309.

As explained above, according to the embodiment of the present invention, each gene expression (cDNA injected) cell of interest can be automatically detected; the fluorescent image, the phase difference image, and the bright-field image of only the detected cell part can be obtained; the protein localization, the morphogenetic change, and the like can be recognized from these images and selected and arranged in the report, which is automatically created, on the basis of information such as the certainty factor of the recognition result. Since the luminance range of each of the images is adjusted so as to facilitate checking the image on a screen, the experimental efficiency is greatly improved by displaying, printing, and saving the image on the screen.

Further, according to the embodiment of the present invention, a fluorescent part in a region corresponding to each cell is specified on the fluorescent image. To do so, a fluorescent pattern and a background pattern are learned beforehand. An "average cell model" is created using the fact that a target is a cell, and a candidate region corresponding to one cell is specified by evaluation of normalized vectors. Further, a profile of one cell can be extracted while referring to the bright-field image or the phase difference image at the same position. Thus, not the entire images but the individual cell regions can be clipped and analyzed, and a result of the analysis can be displayed.

Moreover, according to the embodiment of the present invention, the learning and recognition processing for recognizing the fluorescent pattern and the morphogenetic pattern for each cell can be used. In addition, such a method as an eigenspace method, a subspace method, or a neutral network can be applied. By thus providing the computer with the learning function, the determination result can be automatically output.

The present applicant has actually made trial reports. According to the conventional technique, image data of about 700 megabytes is generated per plate, and a luminance range or the like needs to be adjusted for every visual check. As a result, it takes several hours (three hours or more) to look over the reports (with no time of adding determination results). As for the catalog made by way of trial, by contrast, a capacity of the catalog is about 6 megabytes per plate, so that it takes only a few minutes to look over the catalog and that even determination results can be added.

The image analysis supporting method according to the present embodiment can be a computer-readable program that is prepared beforehand, and the program is realized by executing it by a computer such as a personal computer or a workstation. The program is stored on a computer-readable recording medium, such as an HD, an FD, a CD-ROM, an MO, or a DVD, and the computer executes the program by reading it from the recording medium. The program can be a transmission medium, which can be distributed via a network such as the Internet.

As explained so far, the image analysis supporting method, the computer-readable recording medium, and the image analysis supporting device according to the present invention can promptly and efficiently extract the position of the cell in the image photographed by the microscope and the type of the cell, and automatically display the extraction result for respective cell regions of each cell as a list. The image analysis supporting method, the computer-readable recording medium, and the image analysis supporting device according to the present invention are therefore suited to improve the experimental and analytical efficiencies.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An image analysis supporting method comprising:
accepting an input of a fluorescent image of a plurality of cells adhering to a well of a well plate, and an input of any one of a bright-field image and a phase difference image or both that are equal in field of view to the fluorescent image;
detecting a position of each cell in the fluorescent image;
determining a class of each cell the position of which is detected; and
outputting a list that includes information on the class and an image of each cell that is clipped from any one of the bright-field image and the phase difference image on the basis of the position.

2. The image analysis supporting method according to claim 1, further comprising determining a recognition result for each fluorescent image or each well on the basis of the class of each cell, wherein the list also includes information on the recognition result.

3. The image analysis supporting method according to claim 2, wherein the recognition result is changeable by an operator when the recognition result is incorrect.

4. The image analysis supporting method according to claim 1, wherein the position of each cell in the fluorescent image is detected by calculating a similarity between each candidate region of the cell and any one of an average cell model and an average background model or both.

5. The image analysis supporting method according to claim 4, wherein the position of each cell in the fluorescent image is detected on the basis of a normalized inner product between a feature vector of the candidate region and a main component vector of any one of the average cell model and the average background model or both.

6. The image analysis supporting method according to claim 4, wherein the average cell model includes a main component vector, a distribution value, and an average value of each cell class in a plurality of sample images.

7. The image analysis supporting method according to claim 4, wherein the average background model includes a main component vector, a distribution value, and an average value of each background class in a plurality of sample images.

8. The image analysis supporting method according to claim 1, wherein the class of each cell in the fluorescent image is determined on the basis of a normalized inner product between a feature vector of the cell and an eigenvector of each class.

9. A computer-readable recording medium that stores a computer program that causes a computer to execute:
accepting an input of a fluorescent image of a plurality of cells adhering to a well of a well plate, and an input of any one of a bright-field image and a phase difference image or both that are equal in field of view to the fluorescent image;
detecting a position of each cell in the fluorescent image;
determining a class of each cell the position of which is detected; and
outputting a list that includes information on the class and an image of each cell that is clipped from any one of the bright-field image and the phase difference image on the basis of the position.

10. The computer-readable recording medium according to claim 9, wherein the computer program further causes a computer to execute determining a recognition result for each fluorescent image or each well on the basis of the class of each cell, wherein the list also includes information on the recognition result.

11. An image analysis supporting device comprising:
a first input unit that accepts an input of a fluorescent image of a plurality of cells adhering to a well of a well plate;
a second input unit that accepts an input of any one of a bright-field image and a phase difference image or both that are equal in field of view to the fluorescent image;
a detecting unit that detects a position of each cell in the fluorescent image;
a class determining unit that determines a class of each cell the position of which is detected; and
an output unit that outputs a list that includes information on the class and an image of each cell that is clipped from any one of the bright-field image and the phase difference image on the basis of the position.

12. The image analysis supporting device according to claim 11, further comprising a recognition result determining unit that determines a recognition result for each fluorescent image or each well on the basis of the class of each cell, wherein the list also includes information on the recognition result.

* * * * *